Sept. 23, 1975
J. C. MIKKELSEN
BEGONIA PLANT
Filed Aug. 19, 1974
Plant Pat. 3,787
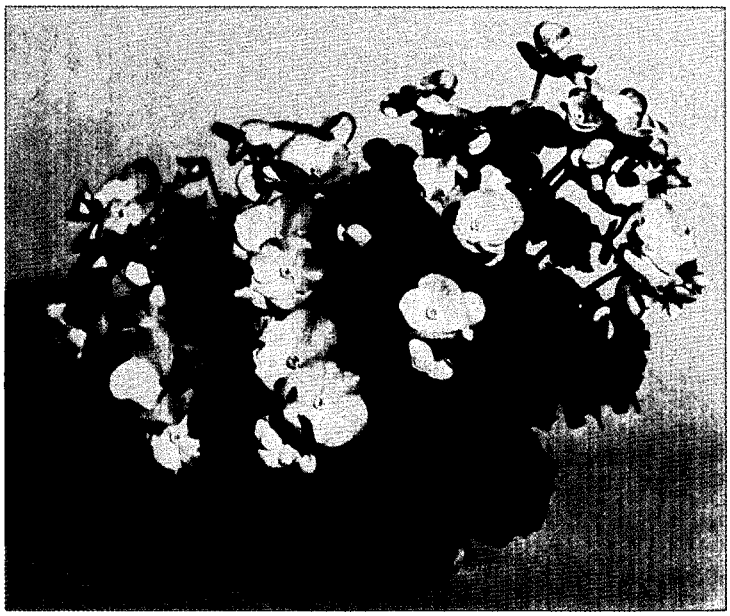

United States Patent

Plant Pat. 3,787
Patented Sept. 23, 1975

3,787
BEGONIA PLANT

James C. Mikkelsen, Ashtabula, Ohio, assignor to Mikkelsens Inc., Ashtabula, Ohio Filed Aug. 19, 1974, Ser. No. 498,868
Int. Cl. A01h 5/00
U.S. Cl. Plt.—68 1 Claim The present invention relates to a new and distinctive variety of begonia plant known by the varietal name Whisper O'Pink and botanically known as *Begonia elatior* (B × *hiemalis*-Fotsch). The new cultivar was discovered by me as a side shoot mutation in a group of stock plants of the parent cultivar Improved Schwabenland Pink, disclosed and claimed in my copending application Ser. No. 392,359, filed Aug. 28, 1973 (now U.S. 3,638). Asexual reproduction by stem and leaf cuttings has reproduced the unique features of the new variety through successive propagations.

The following characteristics distinguish the new begonia from both its parent and other begonias commercially known and used in the floriculture industry:

1. The most distinguishing feature is the soft shell pink color of the flowers. This shade of pink allows the grower a selection of three shades from light pink in Whisper O'Pink, medium pink in Improved Schwabenland Pink and dark pink in Schwabenland Rose.
2. Overall growth habits are less vigorous than parent, the new cultivar being shorter by two to four inches in height.
3. Foliage is typical in general respects to parent and other Schwabenland types except color of leaves are generally a little lighter in color.
4. Initiation of adventitious buds is improved over the parent variety by an average of 1.5–2 more shoots.

The accompanying colored photographic drawing illustrates the new variety with the colors being as true as reasonably possible to obtain in a colored reproduction of this type.

The following is a detailed description of my new begonia variety based on plants produced under commercial practices in Ashtabula, Ohio. Color references are made to the Royal Horticultural Society Colour Chart except where general color terms of ordinary dictionary significance are used.

Parentage: Mutation of Improved Schwabenland Pink.

Propagation: By leaf cuttings rooting in approximately four weeks at 20°–22° C., and developing four to five cm. long adventitious shoots in an additional four weeks.

Rooting habit: Several days faster than parent variety; having fine, dendritic root system.

Plant form: Bushy.

Habit of growth: Upright, vigorous.

Blooming habits: Flowering initiates at terminals of each shoot, alternate on stem and continuous for three to four months and longer.

Blooming season: Normal flowering is late November from summer cuttings. Modern begonia production techniques allow for year round flowering.

Foliage: Is typical for Schwabenland type begonias with average quantity; leaves are alternate, borne at slight angle to stems.

*Size*—Nine to eleven cm. long and seven to eight cm. wide. (Varies with growing conditions.)

*Shape.*—Heart shaped; petiole set back.

*Texture.*—Smooth upper surface, glossy underside.

*Margin.*—Shallow sinuses, close serration in young leaves.

*Color.*—New, top, 146B–C; under, 147C. Mature, top, between 146A–147A; under, 148B.

Disease resistance: Resistance to powdery mildew is comparable to the test variety Schwabenland Red.

Flowers:

*Borne.*—On trusses initiating at terminal ends of shoots, flowers alternating. Flowers are approximately 5 cm. in diameter, being smaller than parent.

*Quantity.*—Number of flowers is average for Schwabenland types.

*Buds.*—Round, flat, expanding to 10–15 mm. in diameter before starting to open. Outside of tepals very light shade of pink to almost white.

*Tepals.*—Medium pink when first opening, 50C, becoming lighter at maturity, 49A.

*Reproductive organs.* — Stamens—Color—14A–B. Pollen—Light greyish yellow. Styles/ovaries—None seen to date.

I claim:

1. A new and distinct cultivar of begonia plant characterized particularly as to uniqueness by its light pink flower color, relatively short growth habit, relatively fast rooting habit, and by its improved characteristics of adventitious bud initiation.

No references cited.

ROBERT E. BAGWILL, Primary Examiner